US006878013B1

(12) United States Patent
Behan

(10) Patent No.: US 6,878,013 B1
(45) Date of Patent: Apr. 12, 2005

(54) CONNECTOR APPARATUS FOR A MEDICAL DEVICE

(76) Inventor: Edgar G. Behan, 3097 Main St., Suite 104, Sugar Hill, GA (US) 30096

(*) Notice: Subject to any disclaimer, the term of this patent is extended or adjusted under 35 U.S.C. 154(b) by 0 days.

(21) Appl. No.: 10/725,687

(22) Filed: Dec. 2, 2003

(51) Int. Cl.[7] .............................................. H01R 24/04
(52) U.S. Cl. ...................... 439/668; 439/335; 439/835; 439/909; 607/116; 607/37
(58) Field of Search ................. 439/668–669, 439/335, 835; 607/37, 116

(56) References Cited

U.S. PATENT DOCUMENTS

| 4,764,132 | A | * | 8/1988 | Stutz, Jr. .................... 607/116 |
| 6,162,101 | A | * | 12/2000 | Fischer et al. ............... 439/729 |
| 6,183,305 | B1 | * | 2/2001 | Doan et al. .................. 439/668 |
| 6,205,358 | B1 | * | 3/2001 | Haeg et al. ................... 607/36 |
| 6,428,336 | B1 | * | 8/2002 | Akerfeldt .................... 439/263 |
| 6,428,368 | B1 | * | 8/2002 | Hawkins et al. ............ 439/271 |
| 6,505,073 | B1 | * | 1/2003 | Gramse ....................... 607/37 |

* cited by examiner

Primary Examiner—Truc Nguyen
(74) Attorney, Agent, or Firm—Hinkle & Bradovich, LLC

(57) ABSTRACT

A connector block assembly for an implantable medical device is described. The connector block generally includes a first and second housing connected to one another forming an indentation that holds a tab. A canted spring or any other electrically conductive displacable configuration is further held within the indentation. The connector block assembly is adapted to be placed within a header, or connector top assembly for an implantable medical device. The tab can be connected to feedthrough wires from the internal circuitry within the medical device. The connector block assembly can interface with a medical electrode to connect a patient's tissue with the medical device.

15 Claims, 7 Drawing Sheets

CONNECTOR APPARATUS FOR A MEDICAL DEVICE

BACKGROUND

I. Field of the Invention

The present invention relates to medical devices and, more particularly, to a connector assembly for an implantable medical device.

II. Description of the Related Art

Implantable medical devices are frequently used to generate an electrical stimulus that is transferred to a target tissue. These devices may also be used to sense electrical signals generated from the target tissues or generated by sensors located at a target location. Some examples of such devices include neurostimulation devices, pacemakers, anti-tachycardia pacers, and defibrillators. Neurostimulation devices are frequently used to artificially stimulate nerves to relieve pain and to treat various neurological disorders whereas pacemakers, anti-tachycardia pacers, and defibrillators are used to stimulate cardiac tissue with an electrical signal in order to correct or modify the rhythm of the heart. Implantable devices generally include a housing which typically hermetically encloses a battery and electronic-circuitry for generating and/or sensing electrical signals. The housing can be implanted subcutaneously. A header, or connector top assembly typically electrically connects an implantable electrode to the housing. The header, or connector top assembly typically includes a connector block assembly secured within the header, or connector top assembly. The electrode typically includes one or more exposed contact surfaces at the distal end that make contact with the tissue or nerve that requires stimulation or sensing. The proximal end of the electrode typically includes corresponding contact surfaces that are mechanically and electrically coupled to the medical device by the header, or connector top assembly. This series of contact surfaces along the proximal connector section, electrically connects the electrode to the connector blocks within the header, or connector top assembly. The proximal connector of the electrode is typically received by the connector assembly through one or more ports in the header. Each of these ports may require a single or multiple contact connector block assemblies, depending on the electrode configuration.

Replacing the implanted device requires the removal of the housing from the patient. This replacement is preferably accomplished without disturbing the associated implanted electrodes. Therefore, it is advantageous that the electrode connection is readily disconnectable. To facilitate this, the proximal connector is typically secured within the header, or connector top assembly with a set screw. A set screw contacting the proximal connector pin is commonly used to permit the electrode to be secured to and removed from the header, or connector top assembly. The header, or connector top assembly is secured and electrically connected to the electronics of the housing to permit the communication of electrical impulses to and/or from the electronics within the housing.

Manufacturing connector assemblies is expensive. The connector blocks of the connector assembly are frequently machined from titanium, stainless steel or other more exotic materials. Machining these materials has limitations. One limitation is the amount of detail capable of being machined on the sealing surface of each connector block. Increased detail could permit configurations of the connector block that would allow variations in block design. These variations could simplify the manufacturing process, could improve function and could reduce the costs of manufacture. Therefore, a need exists for a connector assembly that can be manufactured without the need for machining titanium, stainless steel or other more exotic materials.

Frequently, these connector blocks are individually mounted within preformed cavities in the header, or connector top assembly. These preformed cavities frequently have thin walls that are susceptible to damage. Current methods of manufacture frequently require the formation of these cavities in the injection molded header assemblies to receive the connector blocks. Therefore, a need exists for a header, or connector top assembly that does not require the formation of individual preformed cavities to secure the connector blocks.

Further, titanium, stainless steel and more exotic material connector blocks can result in a relatively heavy connector assembly. Heavy assemblies are not desirable. Therefore, a need exists for a connector assembly unencumbered by the extra weight of the titanium, stainless steel and more exotic material connector blocks typically used in the industry.

SUMMARY

In general. The present invention meets the above-described needs and provides other improvements and advantages that will be recognized by those skilled in the art upon review of the following description and drawings.

In general, in one aspect, the invention features a connector block apparatus adapted to receive a medical electrode having at least one connector contact ring including a canted spring or any other electrically conductive displacable configuration secured to a tab to form electrical contact with the connector contact ring and a first housing connected to a second housing forming an internal indentation when the first and second housings are connected, the tab and the canted spring or any other electrically conductive displacable configuration being held within the indentation.

In one implementation, the tab includes a ring portion and a pad portion, the ring portion being held within the indentation and the pad portion being external to the first and second housings.

In another implementation, the canted spring or any other electrically conductive displacable configuration is held within the interior diameter of the ring portion.

In another implementation, the apparatus further includes a first engaging face on the first housing, the first engaging face having a first protrusion and a first cavity and a second engaging face on the second housing, the second engaging face having a second protrusion and a second cavity, wherein the first protrusion of the first engaging face is received within the second cavity of the second engaging face and the second protrusion of the second engaging face is received within the first cavity of the first engaging face to secure the first housing to the second housing and to secure the tab in an indentation between the first engaging face and the second engaging face.

In another implementation, the apparatus includes a sealing face on each of the housings on a side opposite the engaging faces.

In another aspect, the invention features an implantable medical system including an implantable medical device having a housing and a header, or connector top assembly having a hollow interior and connected to the housing, a connector assembly located within the hollow interior of the header, or connector top assembly, the connector block forming a portion of an elongated cavity and an electrode with a plurality of exposed contact surfaces engaged within the elongated cavity.

In one implementation, the medical device is a neurostimulation device or other form of pulse generator.

In another implementation, the medical device is a pacemaker.

In another implementation, the medical device is a anti-tachycardia pacer.

In another implementation, the medical device is a defibrillator.

In still another implementation, the connector assembly comprises a plurality of connector blocks.

In yet another implementation, each connector block includes a canted spring or any other electrically conductive displacable configuration secured to a tab and a first housing connected in opposition to a second housing, the canted spring or any other electrically conductive displacable configuration and the tab being held within an internal circular indentation formed between the first and second housings.

In another implementation, the first housing includes a first engaging face with the first engaging face having a first protrusion and a first cavity and the second housing includes a second engaging face with the second engaging face having a second protrusion and a second cavity, wherein the first protrusion of the first engaging face is received within the second cavity of the second engaging face and the second protrusion of the second engaging face is received within the first cavity of the first engaging face to secure the first housing to the second housing and to secure the tab between the first engaging face and the second engaging face within the indentation.

In another implementation, the system further includes a sealing face located on either side of each connector block adjacent a corresponding port opening through which the electrode fits.

In another implementation, the system further includes a seal located within the sealing face of adjacent connector blocks of the connector assembly.

In another aspect, the invention features an implantable medical kit, including an implantable medical device having a housing, a header, or connector top assembly connected to a portion of the housing and internal electronics, a connector assembly adapted to be held within the header, or connector top assembly and an electrode adapted to engage with the connector assembly and further adapted to interface with a patient.

In one implementation, the connector assembly comprises one or more connector blocks.

In another implementation, each connector block includes a first and second housing engaged with each other forming an internal indentation including a ring portion of a tab, the ring portion securing a canted spring or any other electrically conductive displacable configuration within the indentation.

In another implementation, the kit further includes a planar pad recession on each connector block including a planar pad portion connected to the ring portion, the planar pad portion being adapted to connect to a feedthrough wire connected to the implantable medical device.

In another implementation, the kit further includes one or more seals adapted to be placed within sealing faces on the connector blocks.

One advantage of the invention is that the weight of the connector block assembly is greatly reduced as compared with present connector block assemblies.

Another advantage of the invention is that the housings of the individual connector blocks can be formed by injection molding as compared to presently machined connector blocks.

Another advantage of the invention is that the tab provides a large planar welding surface to which feedthrough wires from a medical device can be connected to the connector block assembly.

Another advantage of the invention is that each connector block is modularized so that potentially infinite connector blocks can be connected in series.

Other objects, advantages and capabilities of the invention will become apparent from the following description taken in conjunction with the accompanying drawings showing the preferred embodiment of the invention.

DETAILED DESCRIPTION

Figure 1B:
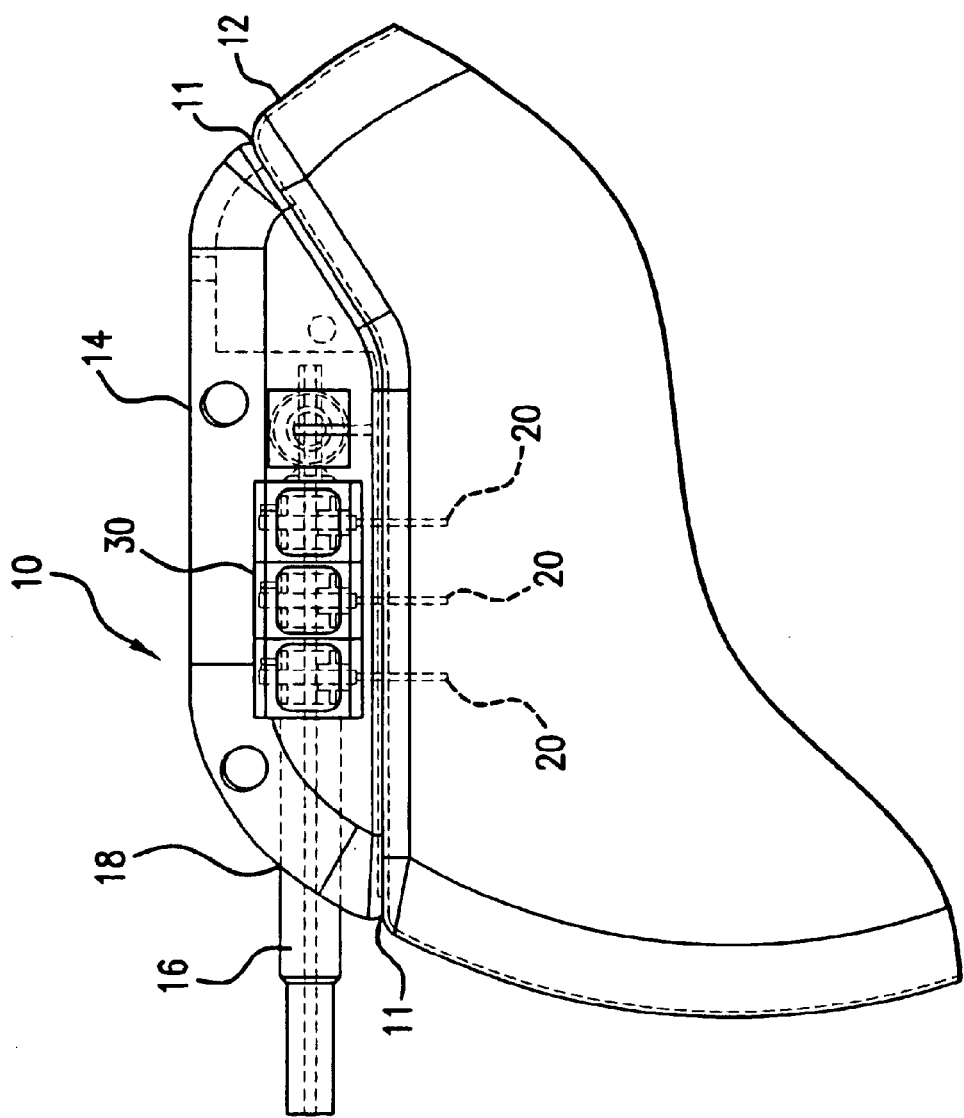
FIG. 1B illustrates a partial side view of the medical device of FIG. 1 with some internal details in phantom.

The embodiments described herein provide a novel apparatus and method for the manufacture of a header, or connector top assembly and connector block assembly for use in a variety of medical applications. The particular embodiments are described below for exemplary purposes only, those skilled in the art will understand how to apply the present invention to the proximal connectors of variety of electrode bodies. Therefore, the appended claims are not intended to be limited to any specific example or embodiment described herein. Further, in the drawings described below, reference numerals are generally repeated where identical or similar elements appear in more than one figure.

Figure 1A:
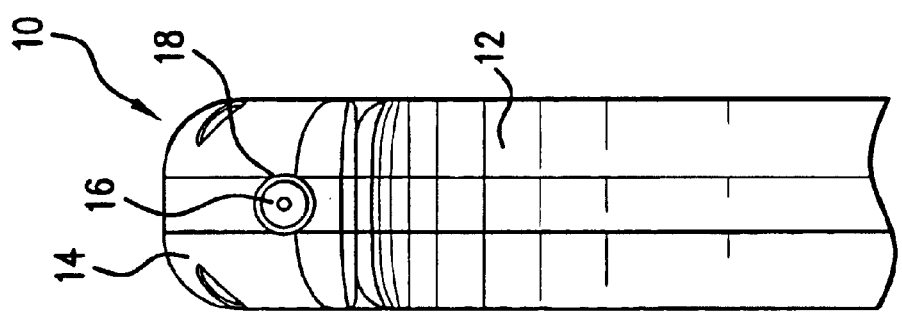
FIG. 1A illustrates a partial front view of an embodiment of a medical device.

Referring to the drawings wherein like reference numerals designate corresponding parts throughout the several figures, reference is made first to FIGS. 1A and 1B that generally illustrate a medical device 10 in accordance with the present invention. Medical device 10 includes a housing or otherwise hermetic enclosure 12 having a header, or connector top assembly 14 secured to a receiving portion 11 of housing 12 and a medical electrode 16 secured within a port 18 of header, or connector top assembly 14. Medical device 10 may be any of a variety of devices used to electrically stimulate tissues in a patient and/or to sense physiological parameters or activity within a patient. The devices can include but are not limited to neurostimulation devices, pacemakers, anti-tachycardia pacers, defibrillators, pulse, pressure or other sensing devices, drug pumps and other pulse generating devices. It is understood that there are many additional devices that can be used with the embodiments described herein. The electrodes 16 typically are connected to one or more tissues in the patient.

Header, or connector top assembly 14 is typically injection molded from a polymeric biocompatible material or other biocompatible material that will be recognized by those skilled in the art. Header, or connector top assembly 14 may be electrically connected to the electronics of housing 12 by one or more feedthrough wires 20. A connector assembly 30 is shown mounted within header, or connector top assembly 14. The feedthrough wires 20 are connected to the connector assembly 30 as discussed in further detail in the description below. It is understood that different types of medical devices have different types of electronics that is appreciated by those skilled in the art.

Figure 2:
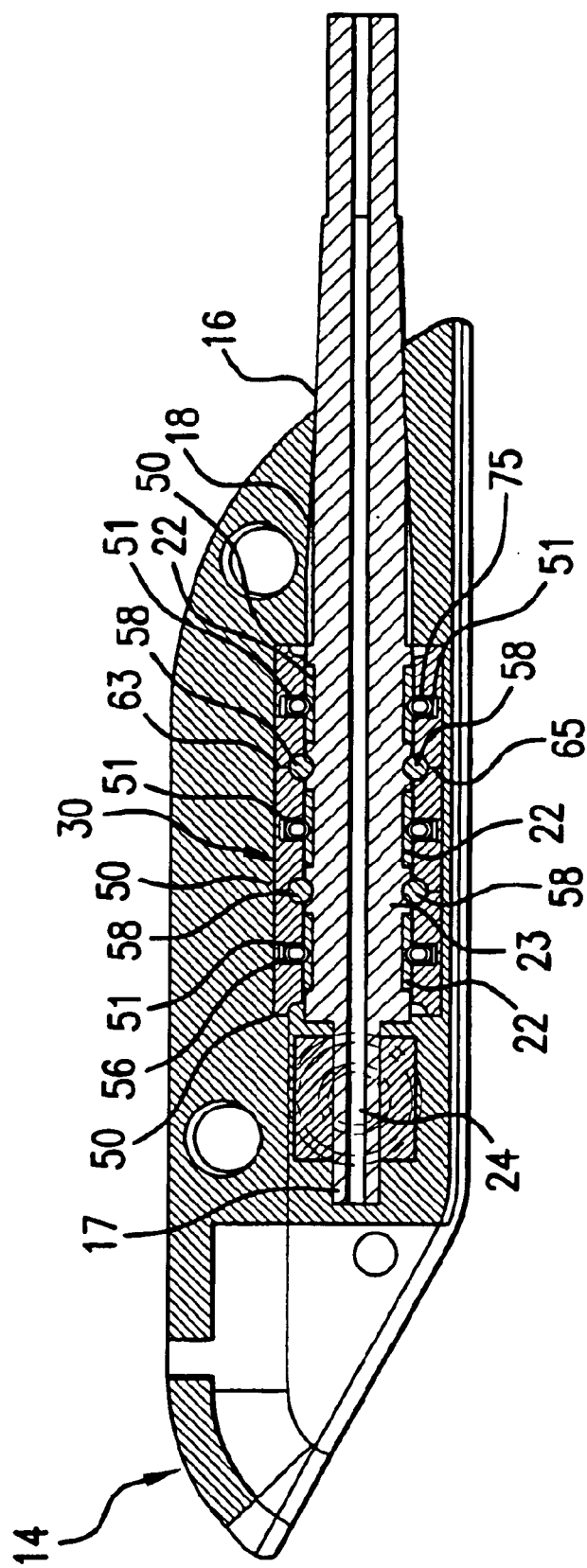
FIG. 2 illustrates a cross-section of an embodiment of a header assembly.
Figure 3:
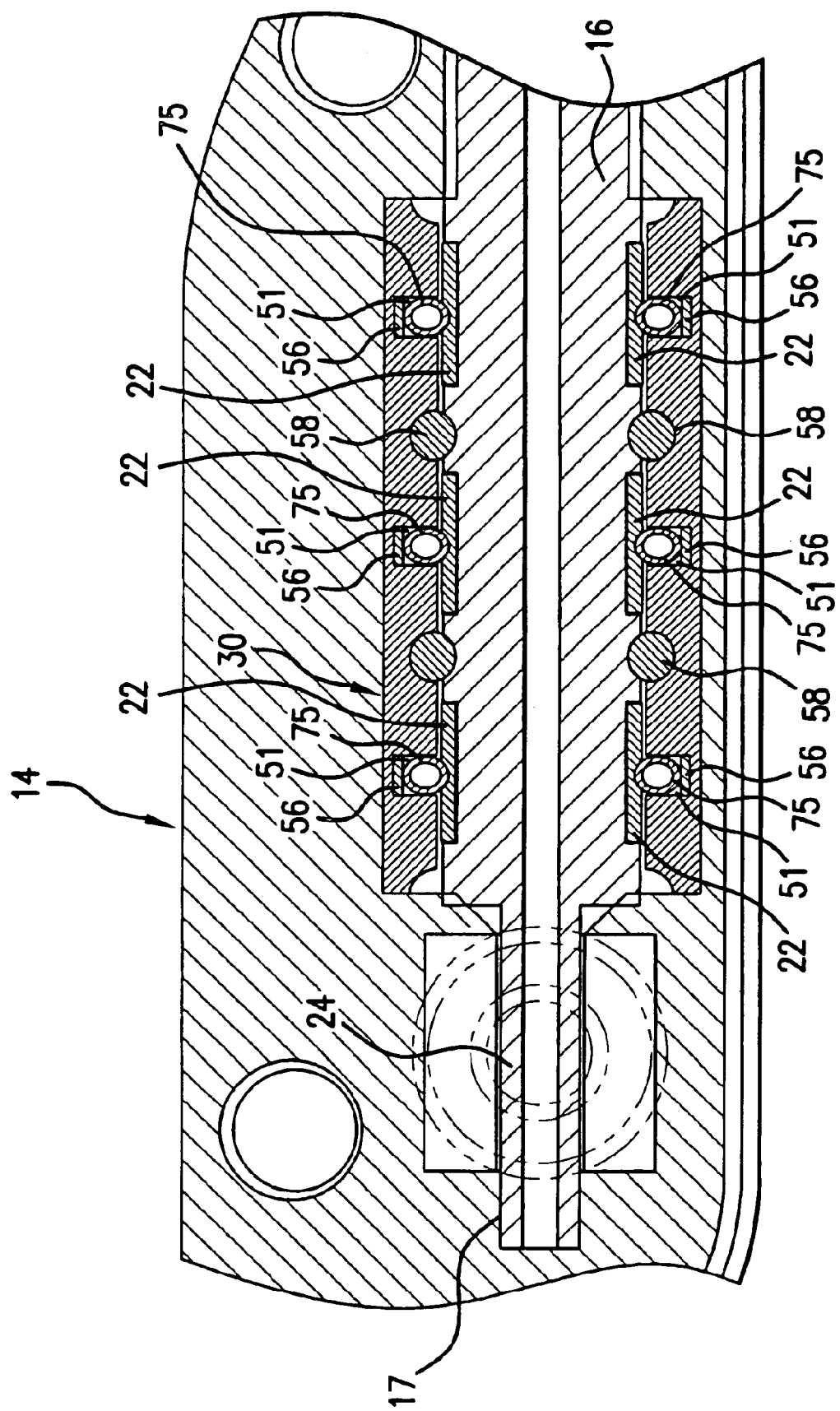
FIG. 3 illustrates a detailed cross-section of the embodiment of a header assembly of FIG. 2.
Figure 4:
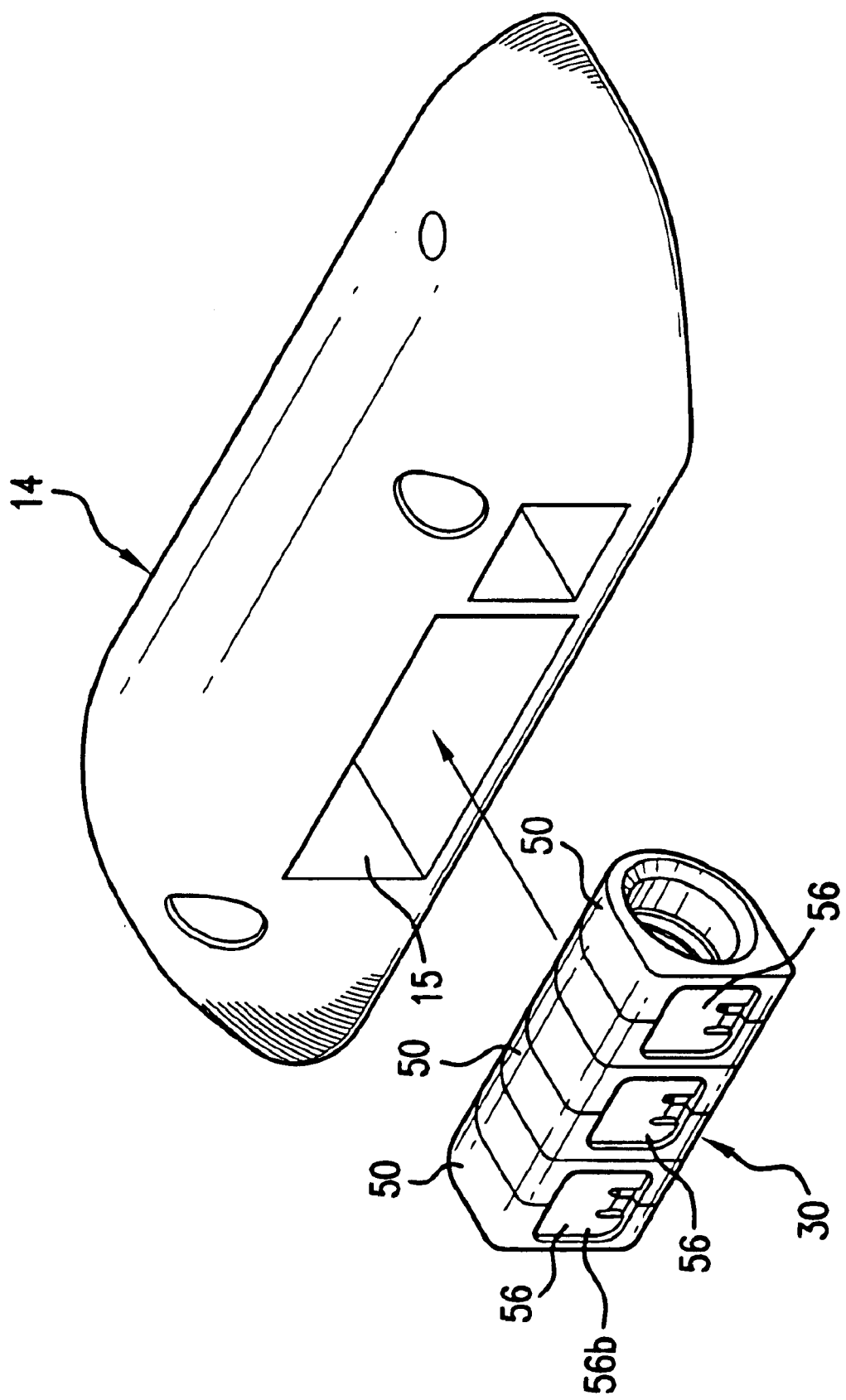
FIG. 4 illustrates an exploded view of an embodiment of a header assembly.

FIGS. 2, 3 and 4 illustrate some details of header, or connector top assembly 14 and medical electrode 16. The medical electrode 16 is generally elongated having a proximal end 17. The proximal end 17 of the electrode 16 typically includes corresponding contact rings 22 that are mechanically and electrically coupled to the medical device by the header, or connector top assembly 14. Medical electrode 16 is received within a port 18 of header, or connector top assembly 14. Port 18 defines a passage through which medical electrode 16 can extend through header, or connector top assembly 14 and through connector assembly 30 to secure medical electrode 16 to header, or connector top assembly 14 and to form electrical contact with the connector contact rings 22 of medical electrode 16. As illustrated, header, or connector top assembly 14 includes a set screw 24 to secure the proximal end 17 of medical electrode 16 within header 14. At least one seal 58 may be used to sealably engage the outer surface of medical electrode 16 within the header, or connector top assembly 14 and more specifically within an inner surface 23 of connector assembly 30. Seal 58 is illustrated as an O-ring for exemplary purposes. It is understood that a variety of seals or seal configurations can be used in other embodiments. The ability to seal between contact surfaces eliminates the need for separate preformed, thin walled cavities typically necessary in current injection molded header.

As described in further detail below, the connector assembly 30 includes one or more interconnectable connector blocks 50 that form a circular indentation 51. A canted spring or any other electrically conductive displacable configuration 75 is located within the indentation 51 and in further electrical contact with a circular portion of a tab 56. The canted spring or any other electrically conductive displacable configuration 75 therefore electrically connects the connector contact rings 22 with its respective metal tab 56. Although a canted spring or any other electrically conductive displacable configuration has been described in the embodiments herein, it is understood by those skilled in the art that other suitable devices can be implemented to make electrical contact as described.

Figure 5:
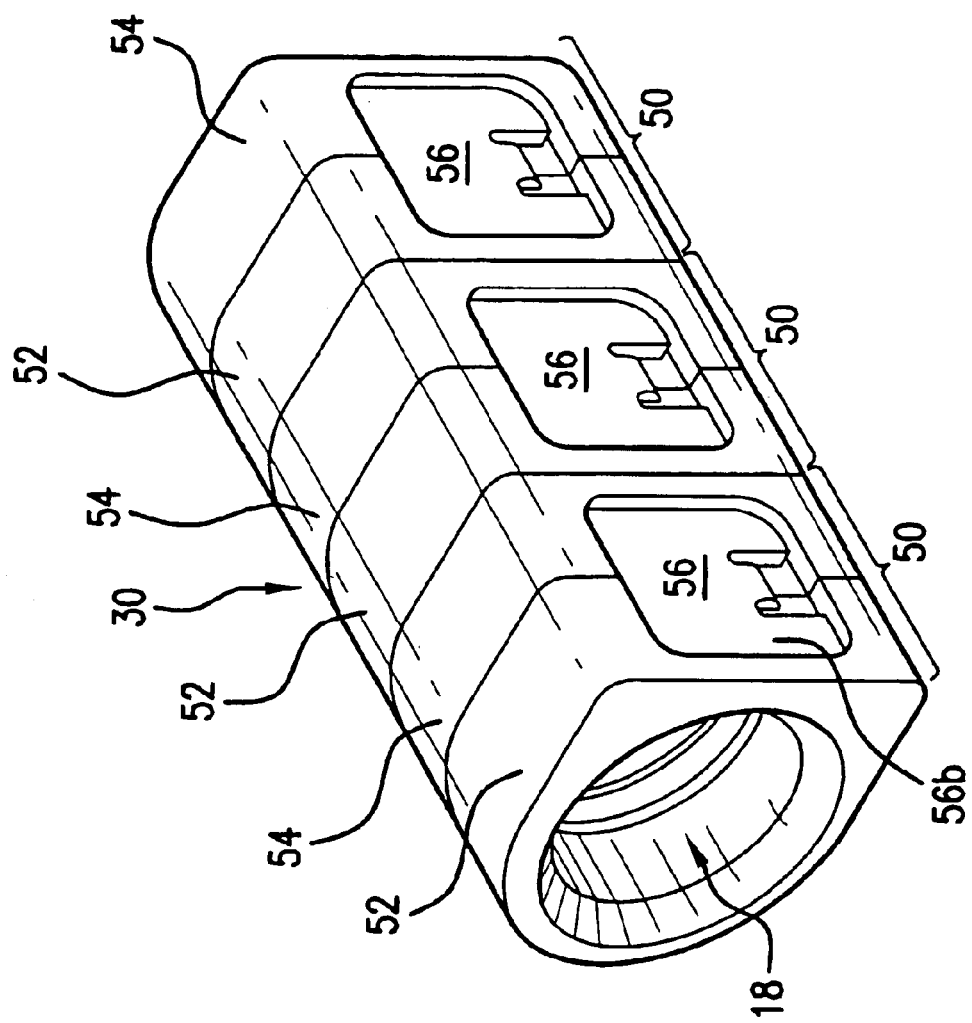
FIG. 5 illustrates a perspective view of an embodiment of a connector assembly.
Figure 6:
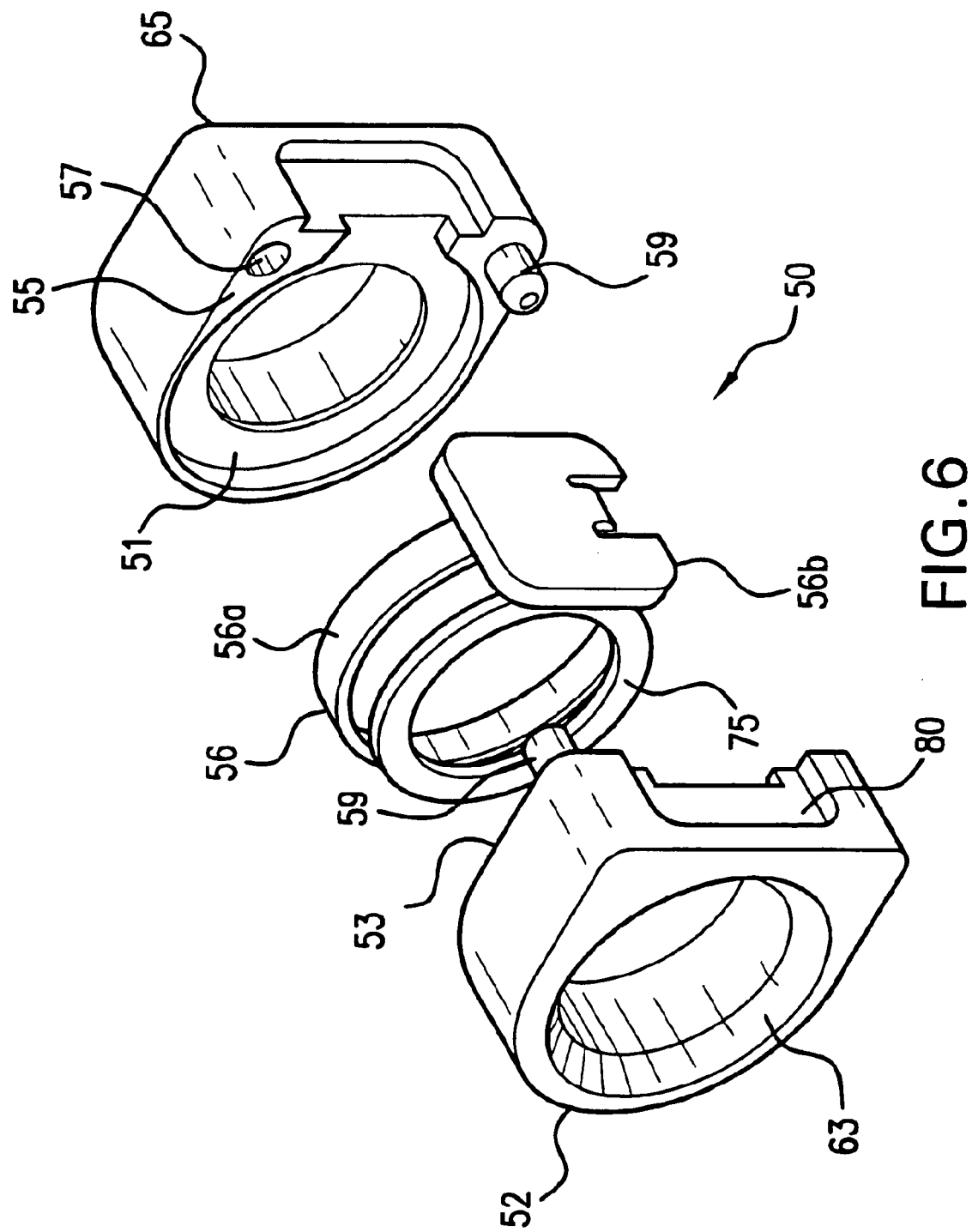
FIG. 6 illustrates an exploded view of the embodiment of a connector assembly.
Figure 7:
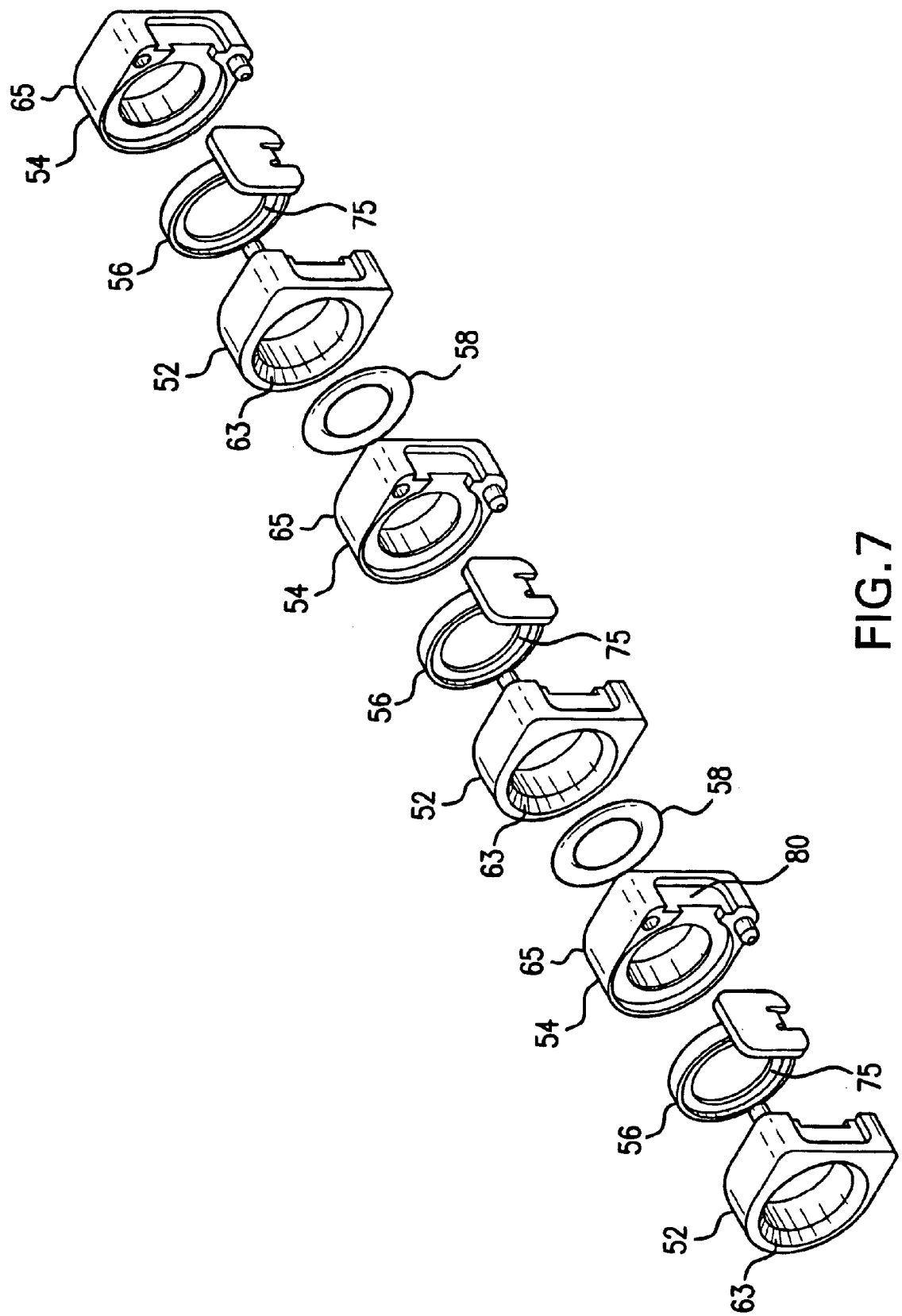
FIG. 7 illustrates a detailed exploded view of an embodiment of a connector assembly of FIG. 5.

FIGS. 4 and 5 illustrate an assembled connector assembly 30 isolated from header, or connector top assembly 14 and FIGS. 6 and 7 illustrated the component parts of a connector assembly 30. The connector assembly 30 is adapted to fit within assembly cavity 15. As mentioned above, the connector assembly 30 can be comprised of one or more connector blocks 50. Each connector block 50 typically includes a first housing 52, a second housing 54, and a contact, illustrated as a metal tab 56 to which the canted spring or any other electrically conductive displacable configuration 75 can be connected. A first engaging face 53 of first housing 52 engages a second engaging face 55 of second housing 54 to secure the metal tab 56 to which a canted spring or any other electrically conductive displacable configuration 75 is connected within indentation 51 that is formed when the engaging faces 53, 55 are met. Metal tab 56 is secured within connector block 50 in indentation 51 such that the connector contact rings 22 of the medical electrode 16 make electrical contact with the canted spring or any other electrically conductive displacable configuration 75, which is in electrical contact with metal tab 56 when the medical electrode 16 is inserted and secured within the port 18. In one embodiment, metal tab 56 to which the canted spring or any other electrically conductive displacable configuration 75 is attached can be constricted so that canted spring or any other electrically conductive displacable configuration 75 receives significant contact pressure thereby providing the necessary contact to the connector contact rings 22 on the electrode 16 without the use of additional mechanical fixation, such as for example a set screw 24.

As illustrated in FIG. 6, first housing 52 and second housing 54 can be identical configurations and placed in opposition. Alternatively, first housing 52 and second housing 54 could be distinct configurations capable of engaging one another to hold an electrical contact. As illustrated, first engaging face 53 and second engaging face 55 each include a cavity 57 and a protrusion 59. When first engaging face 53 engages second engaging face 55 in the illustrated embodiment, protrusion 59 of first engaging face 53 is received within cavity 57 of second engaging face 55 and protrusion 59 of second engaging face 55 is received within cavity 57 of first engaging face 53.

The metal tab 56 includes a ring portion 56a that supports the canted ring 75 that can be permanently fixed to the interior of the ring portion 56a. AS described above, the ring portion sits within he indentation 51. The tab 56 further includes a generally planar pad portion 56b that generally remains external to each connector block 50 and the connector assembly 30, as shown more clearly in FIGS. 4 and 5. The pad portion 56b generally sits within pad recess 80. The planar pad portion 56b can be used to weld or other wise connect the feedthrough wires 20 from the internal circuitry of the medical device 10, which completes the conductive path from the electronics of the medical device 10 to the connector assembly 30. Metal tab 56 can be made from titanium, stainless steel, or of another suitable material as will be recognized by those skilled in the art.

Referring now to FIG. 7, when a plurality of connector blocks 50 comprise the connector assembly 30, first housing 52 may further be provided with a first sealing face 63 and second housing 54 may further be provided with a second sealing face 65. The respective first sealing face 63 and second sealing face 65 of adjacent connector blocks 50 are configured to engage one another in a sealing relationship. As illustrated, first sealing face 63 and second sealing face 65 are configured to secure a seal, shown as an o-ring 58, between adjacent connector blocks 50. When the connector blocks 50 are interconnected with each other, the assembly 30 is formed thereby forming the port 18. In general, each seal 58 is adjacent a corresponding port opening. Adjacent connector blocks 50 may include further elements to secure their first sealing faces 63 and second sealing faces 65 as is recognized by those skilled in the art upon review of the present disclosure.

The connector blocks 50 are modularized so that potentially infinite connector blocks 50 can be added in series. The connector blocks 50 can further be sized to accommodate different sizes of electrodes from medical devices.

First housing 52 and second housing 54 are typically manufactured utilizing injection molding technology. Thus, first housing 52 and second housing 54 are typically manufactured from materials that may be used in injection molding. For example, first housing 52 and second housing 54 may manufactured using poly-ether-ether-ketone (PEEK), polyurethane, polysulfone, or other polymeric materials that will be recognized by those skilled in the art. Injection molded plastic Connector Blocks can be produced in a multi cavity mold, which would have a major cost impact. The details achievable by injection molding the first and second housing are virtually unlimited.

The foregoing is considered as illustrative only of the principles of the invention. Further, various modifications may be made of the invention without departing from the scope thereof and it is desired, therefore, that only such limitations shall be placed thereon as are imposed by the prior art and which are set forth in the appended claims.

What is claimed is:

1. A connector block apparatus to receive a medical electrode having at least one connector contact ring, comprising:
    a canted spring or any other electrically conductive displacable configuration secured to a tab to form electrical contact with the connector contact ring; and
    a first housing connected to a second housing forming an internal indentation when the first and second housings are connected, the tab and the canted spring or any other electrically conductive displacable configuration being held within the indentation;
    wherein the tab includes a ring portion and a pad portion, the ring portion being held within the indentation and the pad portion being external to the first and second housings.

2. The apparatus as claimed in claim 1 wherein the canted spring or any other electrically conductive displacable configuration is held within the interior diameter of the ring portion.

3. The apparatus as claimed in claim 1 further comprising:
    a first engaging face on the first housing, the first engaging face having a first protrusion and a first cavity; and
    a second engaging face on the second housing, the second engaging face having a second protrusion and a second cavity, wherein the first protrusion of the first engaging face is received within the second cavity of the second engaging face and the second protrusion of the second engaging face is received within the first cavity of the first engaging face to secure the first housing to the second housing and to secure the tab in an indentation between the first engaging face and the second engaging face.

4. The apparatus as claimed in claim 3 further comprising a sealing face on each of the housings on a side opposite the engaging faces.

5. An implantable medical system, comprising:
    an implantable medical device having a housing and a header, or connector top assembly having a hollow interior and connected to the housing;
    a connector assembly located within the hollow interior of the header, or connector top assembly, a connector block forming a portion of an elongated cavity; and
    an electrode with a plurality of connector contact rings engaged within the elongated cavity;
    wherein the connector assembly comprises a plurality of connector blocks, each of the connector blocks further comprising:
        a canted spring or any other electrically conductive displacable configuration secured to a tab; and
        a first housing connected in opposition to a second housing, the canted spring or any other electrically conductive displacable configuration and the tab being held within an internal circular indentation formed between the first and second housings.

6. The system as claimed in claim 5 wherein the medical device is a neurostimulation device.

7. The system as claimed in claim 5 wherein the medical device is a pacemaker.

8. The system as claimed in claim 5 wherein the medical device is a anti-tachycardia pacer.

9. The system as claimed in claim 5 wherein the medical device is a defibrillator.

10. The system as claimed in claim 5 wherein the first housing includes a first engaging face with the first engaging face having a first protrusion and a first cavity and the second housing includes a second engaging face with the second engaging face having a second protrusion and a second cavity, wherein the first protrusion of the first engaging face is received within the second cavity of the second engaging face and the second protrusion of the second engaging face is received within the first cavity of the first engaging face to secure the first housing to the second housing and to secure the tab between the first engaging face and the second engaging face within the indentation.

11. The system as claimed in claim 5 further comprising a sealing face located on either side of each connector block adjacent a corresponding port opening through which the electrode fits.

12. The system as claimed in claim 11 further comprising a seal located within the sealing face of adjacent connector blocks of the connector assembly.

13. An implantable medical kit, comprising:
    an implantable medical device having a housing, a header, or connector top assembly connected to a portion of the housing and internal electronics;
    a connector assembly adapted to be held within the header, or connector top assembly; and
    an electrode adapted to engage with the connector assembly and further adapted to interface with a patient;
    wherein the connector assembly comprises one or more connector blocks; and
    wherein each of the connector blocks includes a first and second housing engaged with each other forming an internal indentation including a ring portion of a tab, the ring portion securing a canted spring or any other electrically conductive displacable configuration within the indentation.

14. The kit as claimed in claim 13 further comprising a planar pad recession on each connector block including a planar pad portion connected to the ring portion, the planar pad portion being adapted to connect to a feed through wire connected to the implantable medical device.

15. The kit as claimed in claim 13 further comprising one or more seals adapted to be placed within sealing faces on the connector blocks.

* * * * *